United States Patent
Kleibeuker

(10) Patent No.: US 11,491,335 B2
(45) Date of Patent: Nov. 8, 2022

(54) METHOD AND SYSTEM FOR PROVIDING NEUROMODULATION

(71) Applicant: ONWARD MEDICAL N.V., Eindhoven (NL)

(72) Inventor: Johan Gerard Kleibeuker, Helvoirt (NL)

(73) Assignee: ONWARD MEDICAL N.V., Eindhoven (NL)

( * ) Notice: Subject to any disclaimer, the term of this patent is extended or adjusted under 35 U.S.C. 154(b) by 11 days.

(21) Appl. No.: 17/301,421

(22) Filed: Apr. 2, 2021

(65) Prior Publication Data

US 2021/0308464 A1    Oct. 7, 2021

(30) Foreign Application Priority Data

Apr. 3, 2020    (EP) .................................... 20167870

(51) Int. Cl.
*A61N 1/36*    (2006.01)
(52) U.S. Cl.
CPC ..... *A61N 1/36171* (2013.01); *A61N 1/36062* (2017.08)
(58) Field of Classification Search
CPC .............. A61N 1/36128; A61N 1/3605; A61N 1/36103
See application file for complete search history.

(56) References Cited

U.S. PATENT DOCUMENTS

| 4,398,537 | A | 8/1983 | Holmbo |
| 7,565,195 | B1 * | 7/2009 | Kroll ................. A61N 1/37288 |
| | | | 607/2 |
| 8,543,200 | B2 | 9/2013 | Lane et al. |
| 8,768,481 | B2 | 7/2014 | Lane |
| 2011/0054567 | A1 | 3/2011 | Lane |
| 2011/0054568 | A1 | 3/2011 | Lane |
| 2011/0054570 | A1 | 3/2011 | Lane |
| 2011/0160810 | A1 | 6/2011 | Griffith |
| 2014/0005753 | A1 | 2/2014 | Carbunaru |

OTHER PUBLICATIONS

Extended European Search Report dated Sep. 15, 2020 (7 pages).
Courtine G, et al., Transformation of nonfunctional spinal circuits into functional states after the loss of brain input. Nature neuroscience 12, 1333-1342, (2009).
Wenger N, et al., Spatiotemporal neuromodulation therapies engaging muscle synergies improve motor control after spinal cord injury, Nature Medicine 22, 138-145 (2016).
Capogrosso M, et al., A Computational Model for Epidural Electrical Stimulation of Spinal Sensorimotor Circuits, Journal of Neuroscience Dec. 4, 2013, 33 (49) 19326-19340.
Wenger N, et al., Closed-loop neuromodulation of spinal sensorimotor circuits controls refined locomotion after complete spinal cord injury, in Science Translational Medicine, vol. 6, No. 255, 2014.

* cited by examiner

*Primary Examiner* — Alyssa M Alter
(74) *Attorney, Agent, or Firm* — Finnegan, Henderson, Farabow, Garrett & Dunner, LLP

(57) ABSTRACT

A system for neuromodulation, at least including a timeline definition module configured to define a timeline in which neuromodulation may be provided; A timeline dividing module for dividing the timeline into a series of time slots; several neuromodulation entities, each entity being capable to claim at least one slot exclusively for providing neuromodulation.

13 Claims, 5 Drawing Sheets

| repeat | Frequency |
|---|---|
| 1 | 600.000 |
| 2 | 300.000 |
| 4 | 150.000 |
| 8 | 75.000 |
| 16 | 37.500 |
| 32 | 18.750 |
| 64 | 9.375 |

Fig. 2

| S1 | S2 |  | repeat | Frequency |
|---|---|---|---|---|
| 1 | 1 |  | 1 | 600.000 |
| 2 |  |  | 2 | 300.000 |
|  | 3 |  | 3 | 200.000 |
| 4 |  |  | 4 | 150.000 |
|  | 6 |  | 6 | 100.000 |
| 8 |  |  | 8 | 75.000 |
|  | 12 |  | 12 | 50.000 |
| 16 |  |  | 16 | 37.500 |
|  | 24 |  | 24 | 25.000 |
| 32 |  |  | 32 | 18.750 |
| 64 |  |  | 64 | 9.375 |

Fig. 5

METHOD AND SYSTEM FOR PROVIDING NEUROMODULATION

RELATED APPLICATION DATA

This application claims priority to European Application Number EP 20167870.3, filed Apr. 3, 2020, titled "METHOD AND SYSTEM FOR PROVIDING NEUROMODULATION," the entire disclosure of which is incorporated herein by reference.

TECHNICAL FIELD

The present disclosure relates to a method and system for providing neuromodulation.

BACKGROUND

Epidural electrostimulation (EES) shows promising results for spinal cord injury therapy. The mechanisms are still unclear and under investigation, but EES can both stimulate the leg muscles through the proprioceptive afferent fibers and restore the neuronal network in the spinal cord. EES uses a multi-electrode array placed on the dorsal side of the spinal cord on top of the dura matter. In rats, the combination of serotonergic agonists and EES was able to acutely transform spinal networks from non-functional to highly functional and adaptive states as early as 1 week after injury (Courtine G, et al., Transformation of nonfunctional spinal circuits into functional states after the loss of brain input. Nature neuroscience 12, 1333-1342, (2009)). Moreover, EES also restores voluntary control of locomotion by rewiring the injured spinal cord area (Wenger N, et al., Spatiotemporal neuromodulation therapies engaging muscle synergies improve motor control after spinal cord injury, Nature Medicine 22, 138-145 (2016)).

Because of the complexity of the spinal cord, delivering EES stimulation on the multi-electrode array (lead) implanted is challenging. Computational models were designed and tested on both rats and humans (Capogrosso M, et al., A Computational Model for Epidural Electrical Stimulation of Spinal Sensorimotor Circuits, Journal of Neuroscience 4 Dec. 2013, 33 (49) 19326-19340) to evaluate the neuronal and muscular response to the stimulation, as well as closed-loop neuromodulation systems that refined locomotion after complete spinal cord injury (Wenger N, et al., Closed-loop neuromodulation of spinal sensorimotor circuits controls refined locomotion after complete spinal cord injury, in Science Translational Medicine, vol. 6, num. 255, 2014).

The degree of control required on the neurostimulation restricts largely the available stimulation settings (stimulus space). The stimulation settings must comply with hardware limitations, with requirements on the predictive capability of the system and with safety regulatory norms. For instance, the hardware has a limited power supply, the stimulation outcome (muscle activation) must be controlled, and the electrode chemical stability must be insured independently of the stimulation settings used.

Moreover, each muscle has a different response according to the nerve fibers stimulation settings. Each muscle is associated with nerve fibers and a stimulation area on the implanted lead. This association is called a functional muscle block (FMB), also referred to as stimulation block (SB). The muscle response will vary with the amplitude, but also with the frequency, the pulse shape, or the use of burst of pulses rather than continuous frequency stimulation.

Thus, during a gait cycle, the different FMBs need to be stimulated simultaneously with different pulsed electrical waveforms at different frequencies and amplitudes, sometimes with different pattern of pulses, in order to reproduce a normal-like cycle. In other words, multiple stimulation blocks may exist at the same time. Multiple channels (i.e. multiple FMBs/SBs, pulsed electrical waveforms) variable frequency neurostimulation is harder to control since the neurostimulation's pulses might temporally overlap in time. Overlapping of pulses creates several issues:

It is hardly possible to output 2 pulses on the same electrode simultaneously. If the electrodes are different, the overlapping of 2 pulses will require a higher voltage on the power supply line, and thus will draw out more power from the battery than if they were outputted one after the other. This second point is critical in implantable devices since the battery lifetime is one of the main concerns. The muscle response (outcome) achieved with temporally overlapping pulses will potentially differ from the outcome reached with the same pulses taken separately. Current knowledge of the muscle response induce by spinal cord neurostimulation is limited to orthogonal pulsing.

A stimulation block may be managed by a neuromodulation entity that may require multiple electrodes and at least one pulse generator to implement the required stimulation block. The pulse generator may be an implantable pulse generator or a non-implantable pulse generator. The multiple electrodes may be arranged in an electrode lead and/or electrode array. To stimulate in a controlled fashion and in a secure way a solution to avoid temporal overlap of the pulses and/or stimulation blocks is needed.

One method to avoid overlap of the pulses between pulsed electrical waveforms is to allow only one pulse at a time, and to delay the others. The method, called the "token approach", is described in "US20110054568A1". If two pulse generators want to output a pulse at the same time, one gets the priority and the other is delayed. Other documents describing methods identified as pulse positioning methods include ("U.S. Pat. No. 8,543,200B2", "U.S. Pat. No. 8,768,481B2"). They aim to place the pulses on the timeline in such a way that pulses do not bump into each other, in other words, that overlap is avoided. With these methods, each pulsed electrical waveform will not have a constant frequency, but an instantaneous frequency within a jitter specification. For instance, the requirement can bound the jitter at 10% of the nominal frequency for each pulsed electrical waveform. Thus, at any given instant, a pulsed electrical waveform at the nominal frequency 40 Hz will have its instantaneous frequency between 36 Hz and 44 Hz.

U.S. Pat. No. 4,398,537 describes an independently rate-adjusting multiple channel controller for nerve stimulator transmitter to be used in conjunction with implanted stimulation pulse output unit, wherein an event that two or more trigger signals coincide in the transmitting circuit, the rate control circuit blocks and delays the latter occurring trigger signal with only minor or insignificant effect on a trigger signal rate.

US 2011/0160810 A1 describes a multi-channel neurostimulation system comprising a plurality of electrical terminals configured for being respectively coupled to a plurality of electrodes, stimulation output circuitry including electrical source circuitry of the same polarity configured for generating a polarity of pulse electrical waveforms in a plurality of timing channels. Furthermore, there is a control circuitry configured for instructing the stimulation output circuitry to serially couple the electrical source circuitry to different sets of the electrodes when pulses of the respective pulsed electrical waveforms do not temporarily overlap each other, and for instructing the stimulation output circuitry to couple the electrical source circuitry to a union of the different electrode sets when pulses of the respective pulsed electrical waveforms temporarily overlap each other.

U.S. Pat. No. 8,543,200 B2 describes methods to avoid frequency locking and a multi-channel neurostimulation system using pulse placement. A plurality of pulse electrical waveforms is respectively delivered within a plurality of timing channels of the neurostimulation system, thereby treating the patient. Sets of stimulation pulses within the electrical waveforms that will potentially overlap temporarily are predicted. Each of the potentially overlapping pulse sets is substituted with a replacement stimulation pulse, such that each replacement stimulation pulse is delivered within at least one of the respective timing channels, thereby preventing temporal overlap between the stimulation pulses of the respective electrical waveforms while preventing frequency locking between the timing channels.

SUMMARY

Reference will now be made in detail to exemplary embodiments. Unless otherwise defined, technical or scientific terms have the meaning commonly understood by one of ordinary skill in the art. The disclosed embodiments are described in sufficient detail to enable those skilled in the art to practice the disclosed embodiments. It is to be understood that other embodiments may be utilized and that changes may be made without departing from the scope of the disclosed embodiments. Thus, the materials, methods, and examples are illustrative only and are not intended to be necessarily limiting.

Disclosed embodiments provide a solution for a method and system that can avoid partial and/or full overlap of pulses of neuromodulation/neurostimulation, in particular of multichannel and/or variable neuromodulation/neurostimulation, without blocking, replacing, delaying and/or deleting pulses.

This object is solved by the method provide in the claims. Accordingly, a method for providing neuromodulation comprising at least the following steps: Define a timeline in which neuromodulation may be provided; Divide the timeline into a series of time slots; Provide several neuromodulation entities, each entity being capable to claim at least one slot exclusively for providing neuromodulation.

Disclosed embodiments provide that a temporal overlapping of stimulation events (with stimulation events happening in one or more pulse trains), which can happen in neuromodulation, e.g. multi-channel and/or variable frequency neurostimulation, has to be avoided or minimized to limit the potential adverse impact (e.g. therapeutic side effects, loss of efficacy and/or unsafe situations) on the intended therapy. A timeline is divided into a series of time slots. Each slot can be claimed by a neuromodulation entity (which may manage a stimulation block) for stimulation of a group of electrodes where the electrodes may have different state like anodic, cathodic, floating or grounding. A neuromodulation entity that claimed a time slot may use that reserved time to apply stimulation. This may guarantee that no pulses are colliding (and thus causing therapeutic side effects) due to the exclusivity rights regarding respective time slots.

A stimulation block may be managed by a neuromodulation entity that may require one or multiple electrodes and at least one pulse generator to implement the required stimulation block. The pulse generator may be an implantable pulse generator or a non-implantable pulse generator. The multiple electrodes may be arranged in an electrode lead and/or electrode array. It may be generally possible that two or more neuromodulation entities share one or more electrodes and/or a pulse generator.

A neuromodulation entity may claim a series of time slots equally spaced to deliver stimulation at regular intervals, representing a stimulation frequency. This may be advantageous where repetitive responses to the neuromodulation provided are expected, for example during continuous motion sequences, including but not limited to walking, running, swimming, stepping, running, rowing. Further, this may be advantageous for stimulating autonomic function, smooth muscle function, sphincter function, etc.

Alternatively, a neuromodulation entity may claim a series of time slots not equally spaced, e.g. to implement other features like frequency ramping. This may be advantageous where discontinuous responses to the neuromodulation provided are expected, for example during discontinuous movements, including but not limited to standing up, sitting down, grasping, jumping.

Alternatively, and/or additionally, a neuromodulation entity may claim alternating series to allow other stimulation entities having their series interleaved. This may be advantageous where neuromodulation is provided in order to evoke complex physiological responses with multiple FMBs/SBs included, wherein the responses to the neuromodulation do not have the same duration.

In particular, the neuromodulation may be or may comprise neurostimulation. In general, neurostimulation may be or may comprise electrical neurostimulation. However, alternatively and/or additionally, mechanical neurostimulation and/or pharmacological neurostimulation could be generally possible.

It is generally possible, that electrical neurostimulation comprises transcutaneous electrical stimulation (TENS), epidural electrical stimulation (EES), functional electrical stimulation (FES), intramuscular stimulation (IMS), dorsal root ganglion stimulation, subdural stimulation, cardiac stimulation system, optogenetics, optotrodes, patch-clamp, intra-cellular electrodes and/or extra-cellular electrodes.

Neuromodulation, in particular neurostimulation may be or may comprise central nervous system (CNS) stimulation and/or peripheral nervous system stimulation (PNS). The method may comprise the further step of providing an arbitration unit, wherein by means of the arbitration unit a slot is assigned to one of the claiming neuromodulation entities. In other words, when more than one neuromodulation entity wants to claim a time slot, the arbitration unit may assign the time slot to one of the claiming stimulation entities. It may be understood that also multiple sots may be assigned. The assignment may be random or based on at least one predefined rule or predefined set of rules. Thus, it may be possible that the arbitration unit assigns the slot randomly. This may have the advantage that no neuromodulation entity is preferred compared to other stimulation entities.

Alternatively, and/or additionally, the arbitration unit may assign the slot based on at least one predefined rule or a set of predefined rules. This may have the advantage that a neuromodulation entity with certain priority is preferred compared to other stimulation entities. A predefined rule or a set of predefined rules may use various properties to make the decision which neuromodulation entity may get which time slot or which time slots.

It may be possible to use the stimulation properties of the neuromodulation entity, like amplitude, repetition frequency, pulse width and/or stimulation mode (burst stimulation or no burst stimulation). To implement burst stimulations that do have a higher time resolution then the slots, the stimulation may claim multiple adjacent slots to implement such burst stimulation, for instance, when a neuromodulation entity wants to position a number of pulses on at least two adjacent slots. Only when both claims are honored the neuromodulation entity may continue its stimulation output at the slot boundary between both claimed slots.

Alternatively, and/or additionally, it may be possible to use therapeutic properties, e.g. prioritization of e.g. particular nerve stimulation and/or tonic background stimulation. For instance, a neuromodulation entity for providing stimulation to maintain blood pressure may be prioritized compared to stimulation entities for providing stimulation to evoke motor responses. Further, for instance, a certain motor response may be prioritized compared to at least one other motor response.

Alternatively, and/or additionally, it may be possible to use electronic properties, e.g. prioritization of pulses using less energy. This may be advantageous for the system in order to save energy and/or battery power.

Alternatively, and/or additionally, it may be possible to use spatial properties, e.g. when two or more stimulation entities claim the same time slot but require electrode configurations that do not corrupt each other based on the stimulation properties, e.g. because they are spaced in a certain distance from each other, e.g. on an electrode array, the arbitration unit may honor the claims of each neuromodulation entity.

Alternatively, and/or additionally, it may be possible to use safety properties, e.g. when claims lead to safety issues, like too high charge density, the arbitration unit may use this for arbitration. Alternatively, when grounding is required remaining charge may be removed. This may help to prevent damage of the hardware.

Alternatively, and/or additionally, it may be possible to use starvation, in particular to prevent that claims of a particular neuromodulation entity are refused subsequently.

Apart from arbitration on the time slot, the arbitration unit may additionally and/or alternatively overrule requesting stimulation parameters of a claiming neuromodulation entity such that two claims on the same slot can be honored by using this new stimulation setting. It may be possible that the slots are at least partially equally spaced and/or arranged. In particular, the slots may be at least partially unequally spaced and/or arranged, especially to create, time base, ramping scenarios or the like.

In case that multiple stimulation entities want to operate independently from each other they shall have series (repetitions) that do not collide. Frequencies may be selected such that they may be maximally interleaved without collisions. Aligning input frequency in series of power of two may result in interleaving them such in the free sots without the need of slot arbitration.

Furthermore, the present invention relates to a system for neuromodulation, at least comprising: A timeline definition module configured to define a timeline in which neuromodulation may be provided; A timeline dividing module to divide the timeline into a series of time slots; several neuromodulation entities, each entity being capable to claim at least one slot exclusively for providing neuromodulation.

The system may comprise or may be a neurostimulation system. In particular, the neurostimulation system may be an electrical neurostimulation system, a mechanical stimulation system and/or a pharmacological stimulation system. Thus, the neuromodulation entities may be neurostimulation entities.

It is generally possible, that electrical neurostimulation system comprises a transcutaneous electrical stimulation system (TENS), epidural electrical stimulation system (EES), functional electrical stimulation system (FES), intramuscular stimulation system (IMS), dorsal root ganglion stimulation system, subdural stimulation system, cardiac stimulation system, optogenetics, optotrodes, patch-clamp, intra-cellular electrodes and/or extra-cellular electrodes.

It may be generally possible that the neuromodulation system is a central nervous system (CNS) stimulation system and/or peripheral nervous system stimulation (PNS) system. The system may further comprise an arbitration unit, wherein the arbitration unit is configured to assign at least one slot to one of the claiming neuromodulation entities. The arbitration unit may assign the slot randomly. Alternatively, and/or additionally, the arbitration unit may assign the slot based on at least one predefined rule or a set of predefined rules. In particular the slots may be at least partially equally spaced and/or arranged. In particular, the slots may be at least partially unequally spaced and/or arranged, especially to create ramping scenarios or the like.

In particular, the system may be configured to perform the method according to one of the claims.

Further details and advantages of the present invention shall now be disclosed in connection with the drawings.

BRIEF DESCRIPTION OF THE DRAWINGS

The drawings are not necessarily to scale or exhaustive. Instead, emphasis is generally placed upon illustrating the principles of the inventions described herein. The accompanying drawings, which are incorporated in and constitute a part of this specification, illustrate several embodiments consistent with the disclosure and together with the description, serve to explain the principles of the disclosure. In the drawings:

FIG. 2 depicts an example of frequencies/series selection with the system and method according to the present invention;

FIG. 5 depicts an example of frequencies/series selection with the system and method according to the present invention (cf. FIG. 2), comprising a second series that can be added with minimal impact on the first series.

DETAILED DESCRIPTION

Reference will now be made in detail to exemplary embodiments, discussed with regards to the accompanying drawings. In some instances, the same reference numbers will be used throughout the drawings and the following description to refer to the same or like parts. Unless otherwise defined, technical or scientific terms have the meaning commonly understood by one of ordinary skill in the art. The disclosed embodiments are described in sufficient detail to enable those skilled in the art to practice the disclosed embodiments. It is to be understood that other embodiments may be utilized and that changes may be made without departing from the scope of the disclosed embodiments. Thus, the materials, methods, and examples are illustrative only and are not intended to be necessarily limiting.

Figure 1:
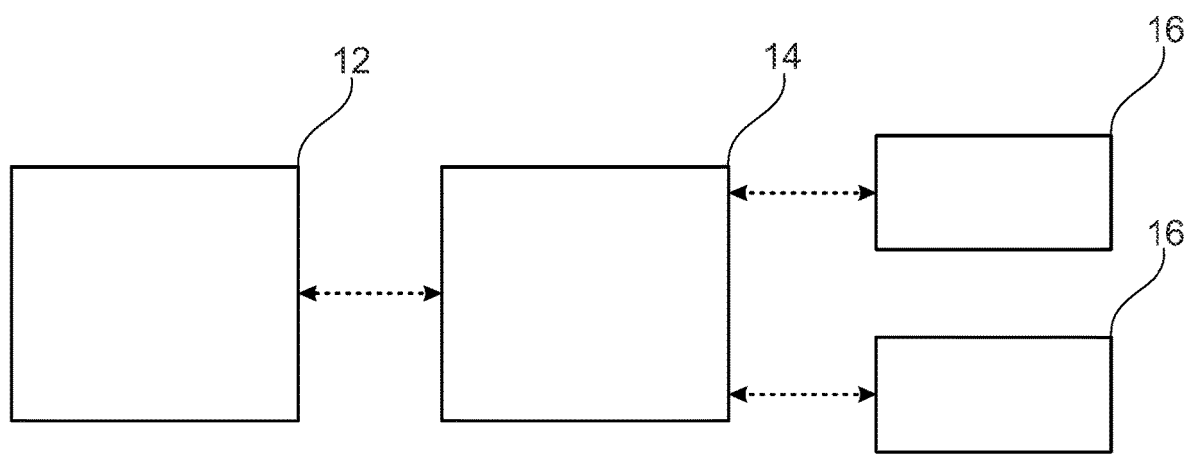
FIG. 1 depicts a schematical overview of an embodiment of the system for neuromodulation according to the present invention, with which the method according to the present invention can be performed.

FIG. 1 shows a schematical overview of an embodiment of the system 10 for neuromodulation, with which the method according to the present invention can be performed. The system 10 comprises a timeline definition module 12. The system 10 further comprises a timeline dividing module 14. The system 10 further comprises two neuromodulation entities 16.

In some embodiments the system 10 could further comprise more than two neuromodulation entities 16. The timeline definition module 12 is connected to the timeline dividing module 14. In this embodiment, the connection between the timeline definition module 12 and the timeline dividing module 14 is a direct connection.

In some embodiments, the connection between the timeline definition module 12 and the timeline dividing module 14 could be an indirect connection. In this embodiment, the connection between the timeline definition module 12 and the timeline dividing module 14 is a bidirectional connection. In some embodiments, the connection between the timeline definition module 12 and the timeline dividing module 14 could be a unidirectional connection (from the timeline definition module 12 to the timeline dividing module 14 or vice versa). The connection between the timeline definition module 12 and the timeline dividing module 14 is a wireless connection. In some embodiments, the connection between the timeline definition module 12 and the timeline dividing module 14 could be a cable bound connection.

The timeline dividing module 14 is connected to the two neuromodulation entities 16. In this embodiment, the connections between the timeline dividing module 14 and the two stimulation entities 16 are direct connections. In some embodiments, the connections between the timeline dividing module 14 and the two stimulation entities 16 could be indirect connections. In this embodiment, the connections between the timeline dividing module 14 and the two stimulation entities 16 are bidirectional connections. In some embodiments, the connections between the timeline definition module 14 and the two stimulation entities 16 could be unidirectional connections (from the timeline definition module 14 to the two stimulation entities 16 or vice versa).

In this embodiment, the connections between the timeline dividing module 14 and the two stimulation entities 16 are wireless connections. In some embodiments, the connection between the timeline dividing module 14 and the two neuromodulation entities 16 could cable bound connections.

The two neuromodulation entities 16 could be connected to each other, via a direct or indirect connection, a unidirectional or bidirectional direction and/or a wireless or cable-bound connection. The timeline definition module 12 defines a timeline T in which neuromodulation may be provided.

The timeline T may be a timeline with a defined start and a defined end or an endless timeline, thus with endless repetitions. In this embodiment, the timeline dividing module 14 divides the timeline T into a series of time slots. In this embodiment, the neuromodulation entities 16 claim at least one slot exclusively for providing neuromodulation. The neuromodulation system 10 is a neurostimulation system 10. Alternatively, and/or additionally, the neuromodulation system 10 could comprise a neurostimulation system 10.

The system 10 could further comprise an arbitration unit 18. The arbitration unit 18 could be connected to each of the other subsystems, i.e. the timeline definition module 12 and/or the timeline dividing module 14 and/or each of the neuromodulation entities 16. Each connection could be a direct or indirect connection, a cable-bound or wireless connection and/or a unidirectional or bidirectional connection. The arbitration unit 18 could be configured to assign at least one slot to one of the claiming neuromodulation entities 16. The arbitration unit 18 could assign the slot randomly. The arbitration unit 18 could assign the slot based on at least one predefined rule or a set of predefined rules. The arbitration unit 18 could assign multiple slots. The slots could be at least partially equally spaced and/or arranged. The slots could be at least partially unequally spaced and/or arranged, especially to create ramping scenarios or the like.

The system 10 could be configured to perform the following method: A method for providing neuromodulation comprising at least the following steps: Define a timeline T in which neuromodulation may be provided; Divide the timeline T into a series of time slots; Provide several neuromodulation entities, 16 each entity 16 being capable to claim at least one slot exclusively for providing neuromodulation. The neuromodulation could comprise or could be neurostimulation.

The method could further comprise the further step of providing an arbitration unit 18, wherein by means of arbitration unit 18 at least one slot is assigned to one of the claiming neuromodulation entities 16. The arbitration unit 18 could assign the slot randomly. Alternatively, and/or additionally, the arbitration unit 18 could assign the slot based on at least one predefined rule or a set of predefined rules. The slots could be at least partially equally spaced and/or arranged. The slots could be at least partially unequally spaced and/or arranged, especially to create, time base, ramping scenarios or the like.

In some embodiments, when the arbitration unit 18 assigns the slot based on at least one predefined rule or a set of predefined rules, the predefined rule or set of predefined rules could use various properties to make the decision which neuromodulation entity 16 may get the time slot.

It could be possible to use the stimulation properties of the neuromodulation entity, like amplitude, repetition frequency, pulse width and/or stimulation mode (burst stimulation or no burst stimulation). Alternatively, and/or additionally, it could be possible to use therapeutic properties, e.g. prioritization of e.g. particular nerve stimulation and/or tonic background stimulation. Alternatively, and/or additionally, it could be possible to use electronic properties, e.g. prioritization of pulses using less energy. Alternatively, and/or additionally, it could be possible to use spatial properties, e.g. when two or more stimulation entities claim the same time slot but require electrode configurations that do not corrupt each other based on the stimulation properties, the arbitration unit may honor both claims. Alternatively. and/or additionally, it could be possible to use safety properties, e.g. when claims lead to safety issues, like too high charge density, the arbitration unit can may use this for arbitration. Alternatively, when grounding is required remaining charge could be removed. Alternatively, and/or additionally, it could be possible to use starvation, in particular to prevent that claims of a particular neuromodulation entity are refused subsequently. In other words, the system 10 disclosed in FIG. 1 is used for performing a method according to embodiments of the present disclosure.

When multiple neuromodulation entities 16 want to operate independently from each other they shall have series (repetitions) that do not collide. Frequencies are selected such that it could be maximally interleaved without collisions. The input frequency in series of power of two is aligned such that they can be interleaved in the free slots without the need of slot arbitration. In this example, 600 equally spaced slots with 1666 microseconds each are assumed. Additionally and/or alternatively, any number and duration of slots could be generally possible.

If one selects the following frequencies (as a power of 2) the following results occur: 600 Hz, 300 Hz, 150 Hz, 75 Hz, 37.5 Hz, 18.75 Hz, 9,375 Hz, etc. Those frequencies have the corresponding repletion frequencies as disclosed in FIG. 2.

Figure 3:
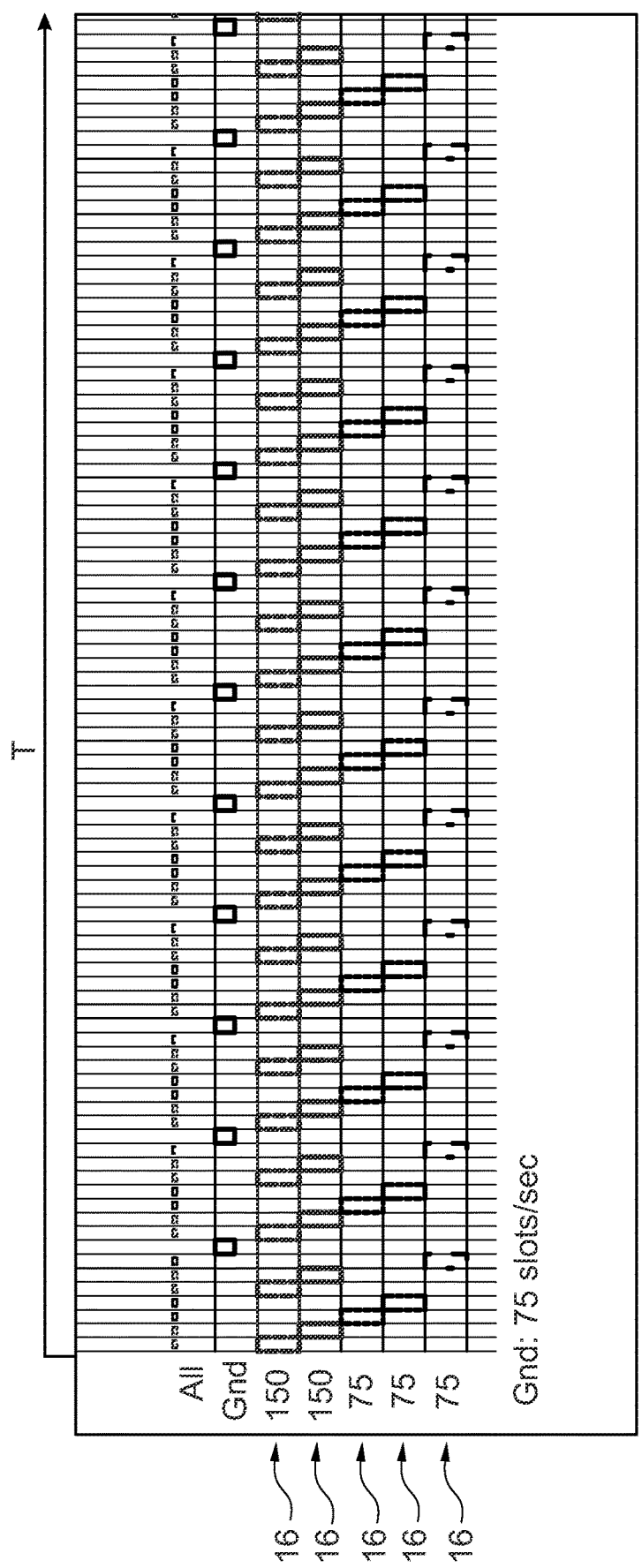
FIG. 3 depicts an example for interleaving frequencies, defined according to the present invention.

With this set it is possible to make any combination as along as the sum of the frequencies do extend beyond 600 Hz: As an example, the following combination could be possible: 1×300 Hz, 1×150 Hz, 3×75 Hz. As another example, the following combination could possible: 2×150 Hz+3×75 Hz, cf. FIG. 3. In particular, FIG. 3 shows a timeline T in which neuromodulation could be provided. The timeline T disclosed in FIG. 3 is provided by the system 10 disclosed in FIG. 1, and the corresponding method. The timeline T is divided into a series of time slots (indicated as space between two adjacent vertical lines). In this embodiment, the slots are equally spaced and/or arranged. In particular, relation to several neuromodulation entities 16 are indicated, and each neuromodulation entity 16 is capable to claim at least one slot exclusively for providing neuromodulation. In other words, several neuromodulation entities 16, each entity 16 being capable to claim several slots exclusively for providing neuromodulation are indicated.

Figure 4:
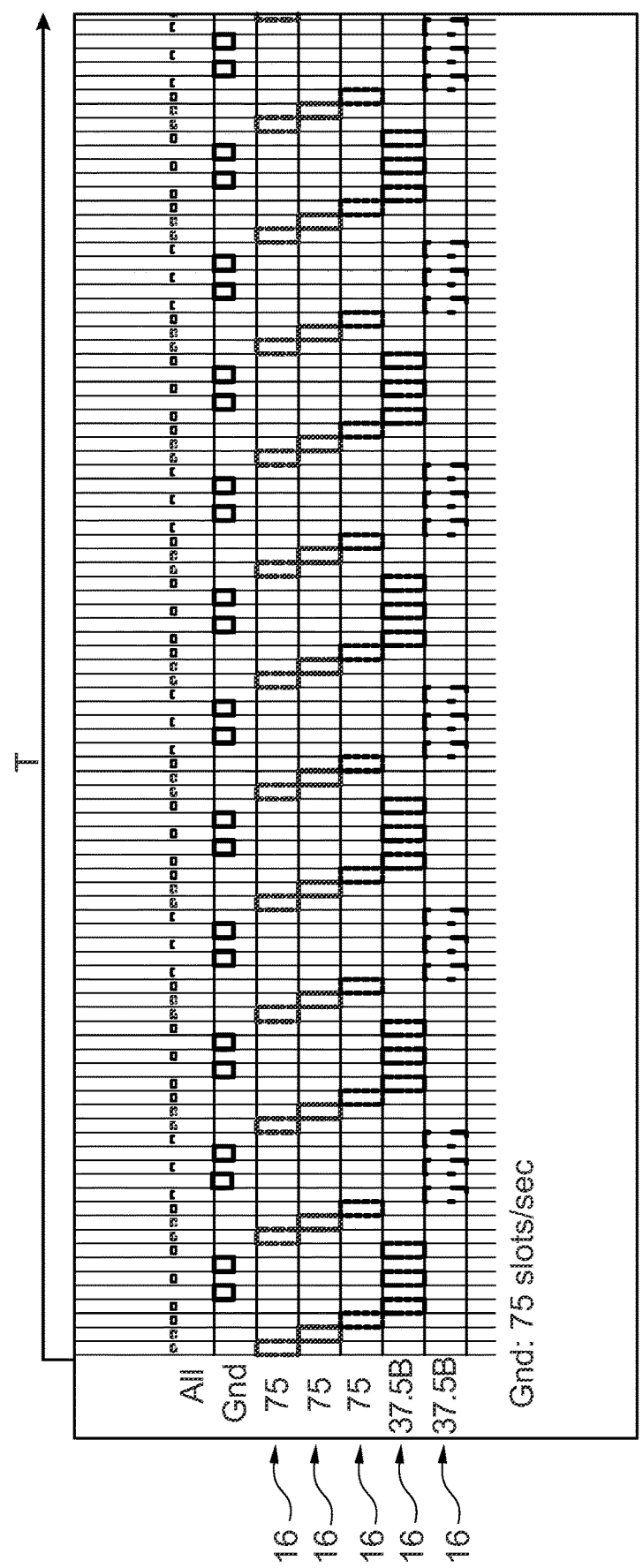
FIG. 4 depicts a further example for interleaving frequencies, defined according to the present invention.

FIG. 4 discloses an example of interleaving two burst frequencies (three pulses every 37.5 Hz, indicated as 37.5B) and three regular frequencies of 75 Hz. In particular, FIG. 4 shows a timeline T in which neuromodulation could be provided. The timeline T disclosed in FIG. 4 is provided by the system 10 disclosed in FIG. 1, and the corresponding method. The timeline T is divided into a series of time slots (indicated as space between two adjacent vertical lines). In this embodiment, the slots are equally spaced and/or arranged.

In particular, relation to several neuromodulation entities 16 are indicated, and each neuromodulation entity 16 is capable to claim at least one slot exclusively for providing neuromodulation. To implement burst stimulations that do have a higher time resolution then the time slots, respective stimulation entities 16 claim multiple adjacent slots to implement such burst stimulation. To accommodate more frequencies between the power of two, a second series can be added to a first series (cf. example shown in FIG. 2), the second series minimally impacting the first series, cf. FIG. 5.

Series 1 S1 and series 2 S2 are shown. Note that not all frequencies need to be part of the series S1, S2. If the bold marked frequencies are excluded, repeats that are multiples of four are provided, which can be interleaved resulting in a set of frequencies that are spaced and can be combined according to their repletion nature.

The foregoing descriptions have been presented for purposes of illustration. They are not exhaustive and are not limited to precise forms or embodiments disclosed. Modifications and adaptations of the embodiments will be apparent from consideration of the specification and practice of the disclosed embodiments. For example, the described implementations include hardware, but systems and methods consistent with the present disclosure can be implemented with hardware and software. In addition, while certain components have been described as being coupled to one another, such components may be integrated with one another or distributed in any suitable fashion.

Moreover, while illustrative embodiments have been described herein, the scope includes any and all embodiments having equivalent elements, modifications, omissions, combinations (e.g., of aspects across various embodiments), adaptations or alterations based on the present disclosure. The elements in the claims are to be interpreted broadly based on the language employed in the claims and not limited to examples described in the present specification or during the prosecution of the application, which examples are to be construed as nonexclusive. Further, the steps of the disclosed methods can be modified in any manner, including reordering steps or inserting or deleting steps.

It should be noted that, the relational terms herein such as "first" and "second" are used only to differentiate an entity or operation from another entity or operation, and do not require or imply any actual relationship or sequence between these entities or operations. Moreover, the words "comprising," "having," "containing," and "including," and other similar forms are intended to be equivalent in meaning and be open ended in that an item or items following any one of these words is not meant to be an exhaustive listing of such item or items, or meant to be limited to only the listed item or items.

The features and advantages of the disclosure are apparent from the detailed specification, and thus, it is intended that the appended claims cover all systems and methods falling within the true spirit and scope of the disclosure. As used herein, the indefinite articles "a" and "an" mean "one or more." Similarly, the use of a plural term does not necessarily denote a plurality unless it is unambiguous in the given context. Further, since numerous modifications and variations will readily occur from studying the present disclosure, it is not desired to limit the disclosure to the exact construction and operation illustrated and described, and accordingly, all suitable modifications and equivalents may be resorted to, falling within the scope of the disclosure.

As used herein, unless specifically stated otherwise, the terms "and/or" and "or" encompass all possible combinations, except where infeasible. For example, if it is stated that a database may include A or B, then, unless specifically stated otherwise or infeasible, the database may include A, or B, or A and B. As a second example, if it is stated that a database may include A, B, or C, then, unless specifically stated otherwise or infeasible, the database may include A, or B, or C, or A and B, or A and C, or B and C, or A and B and C.

It is appreciated that the above-described embodiments can be implemented by hardware, or software (program codes), or a combination of hardware and software. If implemented by software, it may be stored in the above-described computer-readable media. The software, when executed by the processor can perform the disclosed methods. The computing units and other functional units described in this disclosure can be implemented by hardware, or software, or a combination of hardware and software. One of ordinary skill in the art will also understand that multiple ones of the above-described modules/units may be combined as one module/unit, and each of the above-described modules/units may be further divided into a plurality of sub-modules/sub-units.

In the foregoing specification, embodiments have been described with reference to numerous specific details that can vary from implementation to implementation. Certain adaptations and modifications of the described embodiments can be made. Other embodiments can be apparent to those skilled in the art from consideration of the specification and practice of the invention disclosed herein. It is intended that the specification and examples be considered as exemplary only, with a true scope and spirit of the invention being indicated by the following claims. It is also intended that the sequence of steps shown in figures are only for illustrative purposes and are not intended to be limited to any particular sequence of steps. As such, those skilled in the art can appreciate that these steps can be performed in a different order while implementing the same method.

The invention claimed is:

1. A method for providing neuromodulation comprising:
defining a timeline in which neuromodulation may be provided;
dividing the timeline into a series of time slots;
providing a plurality of neuromodulation entities, each of the plurality of neuromodulation entities being capable to claim at least one slot exclusively for providing neuromodulation;
wherein each of the plurality of neuromodulation entities manages a stimulation block;
providing an arbitration unit configured to honor the claim of the neuromodulation entities by assigning at least one of the series of time slots to the claiming neuromodulation entities;
when two or more of the plurality of neuromodulation entities claim a same time slot of the series of time slots but require configurations that do not corrupt each other, honoring the claims of each neuromodulation entities.

2. The method according to claim 1, wherein the neuromodulation comprises or is neurostimulation.

3. The method of claim 1, wherein the arbitration unit assigns the slot randomly.

4. The method of claim 1, wherein the arbitration unit assigns the slot based on at least one predefined rule or a set of predefined rules.

5. The method according to claim 1, wherein the slots are at least partially equally spaced.

6. The method according to claim 1, wherein the slots are at least partially unequally spaced or arranged.

7. A system for neuromodulation, comprising:
a timeline definition module configured to define a timeline in which neuromodulation may be provided;
a timeline dividing module to divide the timeline into a series of time slots;
a plurality of neuromodulation entities, each of the plurality of neuromodulation entities being capable to claim at least one slot exclusively for providing neuromodulation;
wherein each of the plurality of neuromodulation entities manages a stimulation block;
an arbitration unit configured to honor the claim of the neuromodulation entities by assigning at least one of the series of time slots to the claiming neuromodulation entities, and when two or more of the plurality of neuromodulation entities claim a same time slot of the series of time slots but require configurations that do not corrupt each other, honoring the claims of each neuromodulation entities.

8. The system according to claim 7, wherein the system for neuromodulation comprises or is a system for neurostimulation.

9. The system of claim 7, wherein the arbitration unit assigns the slot randomly.

10. The system of claim 7, wherein the arbitration unit assigns the slot based on at least one predefined rule or a set of predefined rules.

11. The system according to claim 7, wherein the slots are at least partially equally spaced.

12. The system according to claim 7, wherein the slots are at least partially unequally spaced to create ramping scenarios.

13. The system according to claim 7, wherein the system is configured to perform the method according to claim 1.

* * * * *

UNITED STATES PATENT AND TRADEMARK OFFICE
CERTIFICATE OF CORRECTION

PATENT NO. : 11,491,335 B2
APPLICATION NO. : 17/301421
DATED : November 8, 2022
INVENTOR(S) : Johan Gerard Kleibeuker It is certified that error appears in the above-identified patent and that said Letters Patent is hereby corrected as shown below:

On the Title Page

Item (30) Foreign Application Priority Data, "20167870" should read as --20167870.3--.

Signed and Sealed this
Seventh Day of March, 2023

Katherine Kelly Vidal
*Director of the United States Patent and Trademark Office*